(12) United States Patent  
Eastgate et al.

(10) Patent No.: US 8,889,869 B2  
(45) Date of Patent: Nov. 18, 2014

(54) METHODS FOR THE PREPARATION OF HIV ATTACHMENT INHIBITOR PIPERAZINE PRODRUG COMPOUND

(71) Applicant: Bristol-Myers Squibb Company, Princeton, NJ (US)

(72) Inventors: Martin D. Eastgate, Trenton, NJ (US); Michael S. Bultman, Union City, NJ (US); Ke Chen, East Brunswick, NJ (US); Dayne Dustan Fanfair, East Windsor, NJ (US); Richard J. Fox, Yardley, PA (US); Thomas E. La Cruz, North Brunswick, NJ (US); Boguslaw M. Mudryk, East Windsor, NJ (US); Christina Ann Risatti, Princeton, NJ (US); James H. Simpson, Hillsborough, NJ (US); Maxime C. Soumeillant, Hamilton Square, NJ (US); Jonathan Clive Tripp, Westfield, NJ (US); Yi Xiao, Fanwood, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 31 days.

(21) Appl. No.: 13/760,526

(22) Filed: Feb. 6, 2013

(65) Prior Publication Data  
US 2013/0203992 A1     Aug. 8, 2013

Related U.S. Application Data

(60) Provisional application No. 61/596,362, filed on Feb. 8, 2012.

(51) Int. Cl.  
*C07D 471/04*     (2006.01)  
*C07C 213/08*     (2006.01)  
*C07F 9/6561*     (2006.01)

(52) U.S. Cl.  
CPC ............. *C07F 9/6561* (2013.01); *C07C 213/08* (2013.01); *C07D 471/04* (2013.01)  
USPC ........................................................ 546/113

(58) Field of Classification Search  
CPC .................................................... C07D 471/04  
See application file for complete search history.

(56) References Cited

U.S. PATENT DOCUMENTS

| 7,354,924 | B2 | 4/2008 | Wang et al. |
| 7,745,625 | B2 | 6/2010 | Ueda et al. |
| 8,436,168 | B2 | 5/2013 | Tripp et al. |

FOREIGN PATENT DOCUMENTS

| WO | WO 02/062423 | 8/2002 |
| WO | WO 2007/127731 | 11/2007 |
| WO | WO 2009/158394 | 12/2009 |

OTHER PUBLICATIONS

Mérour, J.-Y. et al., "Synthesis and Reactivity of 7-Azaindoles (1H-Pyrrolo[2,3-b]pyridine)", Current Organic Chemistry, vol. 5, No. 5, pp. 471-506 (2001).

*Primary Examiner* — Andrew D Kosar  
*Assistant Examiner* — John S Kenyon  
(74) *Attorney, Agent, or Firm* — John F. Levis

(57) ABSTRACT

A method for making the compound

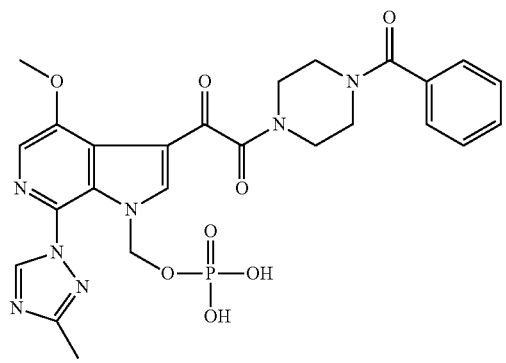

is set forth utilizing the starting material

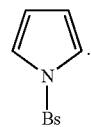

8 Claims, No Drawings

METHODS FOR THE PREPARATION OF HIV ATTACHMENT INHIBITOR PIPERAZINE PRODRUG COMPOUND

CROSS REFERENCE TO RELATED APPLICATION

This non-provisional application claims the benefit of U.S. Provisional Application Ser. No. 61/596,362 filed Feb. 8, 2012.

FIELD OF THE INVENTION

The invention relates to methods of making HIV attachment inhibitor compounds useful as antivirals, and in particular, to methods of making the piperazine prodrug compound identified as 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine. The invention also relates to the compounds, including intermediates, obtained by the processes herein set forth.

BACKGROUND OF THE INVENTION

HIV-1 (human immunodeficiency virus-1) infection remains a major medical problem, with tens of millions of people still infected worldwide at the end of 2011. The number of cases of HIV and AIDS (acquired immunodeficiency syndrome) has risen rapidly. In 2005, for example, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or Retrovir®), didanosine (or Videx®), stavudine (or Zerit®), lamivudine (or 3TC or Epivir®), zalcitabine (or DDC or Hivid®), abacavir succinate (or Ziagen®), Tenofovir disoproxil fumarate salt (or Viread®), emtricitabine (or FTC or Emtriva®), Combivir® (contains-3TC plus AZT), Trizivir® (contains abacavir, lamivudine, and zidovudine), Epzicom® (contains abacavir and lamivudine), Truvada® (contains Viread® and Emtriva®); non-nucleoside reverse transcriptase inhibitors: nevirapine (or Viramune®), delavirdine (or Rescriptor) and efavirenz (or Sustiva®), Atripla® (Truvada®+Sustiva®), and etravirine, and peptidomimetic protease inhibitors or approved formulations: saquinavir, indinavir, ritonavir, nelfinavir, amprenavir, lopinavir, Kaletra® (lopinavir and Ritonavir), darunavir, atazanavir (Reyataz®), and tipranavir (Aptivus®), and integrase inhibitors such as raltegravir (Isentress®), and entry inhibitors such as enfuvirtide (T-20) (Fuzeon®) and maraviroc (Selzentry®).

In addition, HIV attachment inhibitors are a novel subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents.

One HIV attachment inhibitor compound, in particular, has now shown considerable prowess against HIV. This compound is identified as 1-(4-benzoyl-piperazin-1-yl)-2-[4-methoxy-7-(3-methyl-[1,2,4]triazol-1-yl)-1H-pyrralo[2,3-c]pyridine-3-yl]-ethane-1,2-dione, and is set forth and described in U.S. Pat. No. 7,354,924, which is incorporated herein in its entirety:

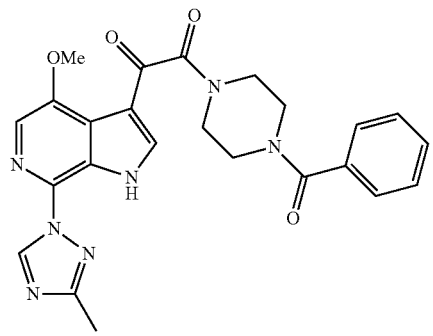

The above compound is the parent compound of the prodrug known as 1-benzoyl-4-[2-[4-methoxy-7-(3-methyl-1H-1,2,4-triazol-1-yl)-1-[(phosphonooxy)methyl]-1H-pyrrolo[2,3-c]pyridin-3-yl]-1,2-dioxoethyl]-piperazine. It is set forth and described in U.S. Pat. No. 7,745,625, which is incorporated by reference herein it its entirety. The compound is represented by the formula below:

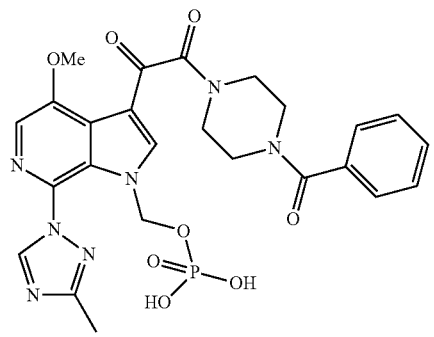

Various methods for making this prodrug compound have been set forth, including those detailed in the '625 reference. In particular, the '625 reference includes various methods for acylation, alkylation and phosphorylation. Another patent reference, U.S. Ser. No. 13/359,708 filed Jan. 27, 2012, entitled "METHODS OF MAKING HIV ATTACHMENT INHIBITOR PRODRUG COMPOUND AND INTERMEDIATES", also details various procedures for making the piperazine prodrug compound. These include a multi-step process which uses the compound

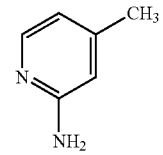

a starting material, which is subsequently brominated, and then nitrated. Further on, a triazolyl moiety is added to the compound before further attaching the piperazine moiety separated by dual carbonyl groups.

What is now needed in the art are new methods of making the piperazine prodrug compound which is useful against HIV. These methods should provide a further comprehensive and efficient means for making the prodrug molecule, both in terms of overall yield and material throughput.

SUMMARY OF THE INVENTION

In a first embodiment, the invention provides a process for preparing the compound of Formula I

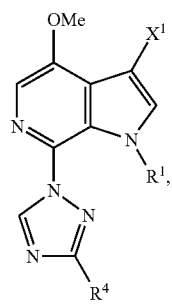
(I)

which comprises:
(a) reacting the compound 1

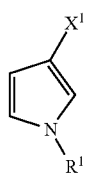
1 with the acid chloride compound

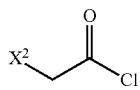

to form the compound 2

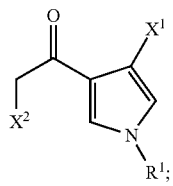
2 and then
(b) contacting the compound 2 with a di-substituted amine $(R^2)_2NH$ in base to produce the compound 3

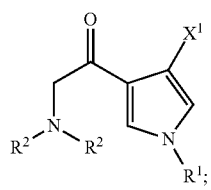
3 and thereafter (c) reacting the compound 3 with the dihydroxy compound HO∩OH in acid solution, wherein the linker between the hydroxyl groups is $C_1$-$C_6$ alkyl, to yield the comound 4

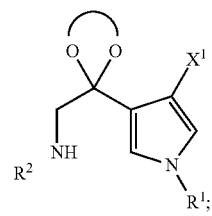
4 and
(d) reacting the compound 4 with the compound

in acid to produce the compound 5

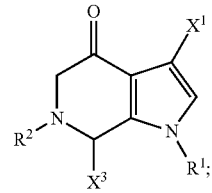
5

(e) contacting the compound 5 with Me-$X^4$ in base or MeO—$R^3$ in acid to produce the compound 6

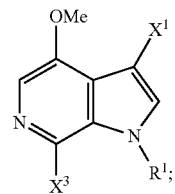
6 and
(f) then performing an oxidation reaction on compound 6 using [O] to yield the compound 7

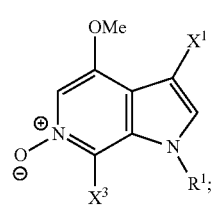
7 and (g) adding the triazolyl group

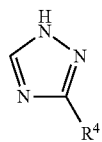
8 to compound 7, and then conducting a functional group interconversion reaction, to obtain the compound (I) above, wherein:

$R^1$=—H, -Boc, -Piv, —SO$_2$Aryl, —CH$_2$SAryl, —CH$_2$OP(O)(OR)$_2$, —CH$_2$OR, —CH$_2$Aryl;

$R^2$=each independently —H, —CO$_2$R, —SO$_2$Aryl, —CHO;

$R^3$ and $R^4$=each independently —H, —CO$_2$R, —CH$_2$SR, —CH$_2$OR, —CH(OR)$_2$, —CH(OR)(NR$_2$), —CH(NR$_2$)$_2$, (C$_1$-C$_6$) alkyl;

R=each independently —H, —C$_1$-C$_6$ alkyl, -aryl, —CH$_2$Aryl;

$X^1$=—H, —Cl, —Br, —I,

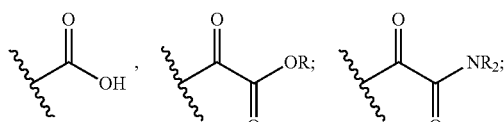

$X^2$=—Cl, —Br, —I, —N(R$^2$)$_2$, —OSO$_2$R;

$X^3$=each independently —H, —OR, —NR$_2$—Cl, —Br, —I, —SR, —SO$_2$R, —SO$_3$R, —SR$_2$;

and $X^4$=—Cl, —Br, —I, OTs (tosylate group), +NR$_3$, -pyridium, and

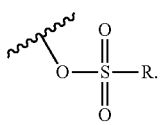

In this embodiment, it is preferred that $R^1$ is —SO$_2$Aryl. Aryl herein is preferably phenyl. It is also preferred that $X^1$ is —H. Additionally, it is preferred that $X^3$ is —H. It is also preferred that the dihydroxy compound is ethylene glycol.

In a further embodiment, the invention is directed to a process for preparing the compound of Formula I

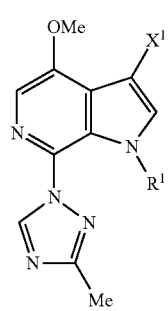
(I)

which comprises:

(a) reacting the compound 1

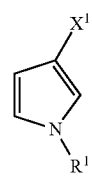
1 with the acid chloride compound

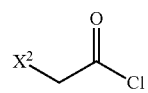

to form the compound 2

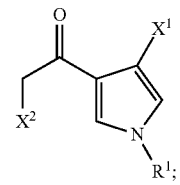
2 and then (b) contacting the compound 2 with a di-substituted amine (R$^2$)$_2$NH in base to produce the compound 3

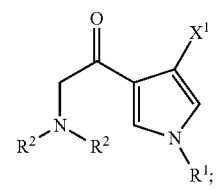
3 and thereafter (c) reacting the compound 3 with the dihydroxy compound

in acid solution, wherein the linker between the hydroxyl groups is C$_1$-C$_6$ alkyl, to yield the compound 4

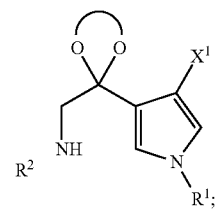
4 and
(d) reacting the compound 4 with the compound

5 in acid to produce the compound 5

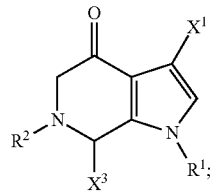

5

(e) contacting the compound 5 with Me-$X^4$ in base or MeO—$R^3$ in acid to produce the compound 6

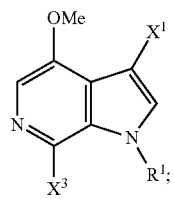

6 and
(f) then performing an oxidation reaction on compound 6 using [O] to yield the compound

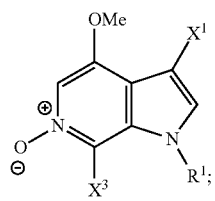

7 and
(g) adding the triazolyl group 9

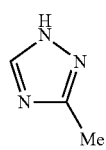

9 to compound 7, to obtain the compound (I) above wherein:
$R^1$=—H, -Boc, -Piv, —$SO_2$Aryl, —$CH_2$SAryl, —$CH_2$OP(O)(OR)$_2$, —$CH_2$OR, —$CH_2$Aryl;
$R^2$=each independently —H, —$CO_2$R, —$SO_2$Aryl, —CHO;
$R^3$=—H, —$CO_2$R, —$CH_2$SR, —$CH_2$OR, —CH(OR)$_2$, —CH(OR)(NR$_2$), —CH(NR$_2$)$_2$;

R=each independently —H, —$C_1$-$C_6$ alkyl, -aryl, —$CH_2$Aryl;
$X^1$=—H, —Cl, —Br, —I,

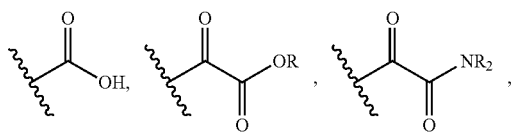

$X^2$=—Cl, —Br, —I, —N(R$^2$)$_2$, —$OSO_2$R;
$X^3$=each independently —H, —OR, —NR$_2$, Cl, —Br, —I, —SR, —$SO_2$R, —$SO_3$R, —$SR_2^+$;
and $X^4$=—Cl, —Br, —I, -OTs, +NR$_3$, -pyridium, and

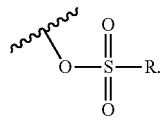

In this further embodiment, it is preferred that $R^1$ is —$SO_2$Aryl. Aryl herein is preferably phenyl. It is also preferred that $X^1$ is —H. Additionally, it is preferred that $X^3$ is —H. It is also preferred that the dihydroxy compound is ethylene glycol.

In another embodiment, there is provided a process for the preparation of the compound of Formula I

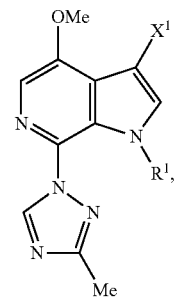

I which comprises:
(a) reacting the compound 1

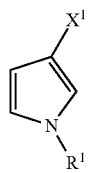

1 with the acid chloride compound

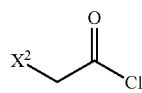

to form the compound 2

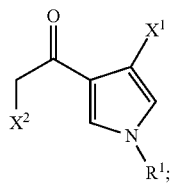
2 and then
(b) contacting the compound 2 with a di-substituted amine $(R^2)_2NH$ in base to produce the compound 3

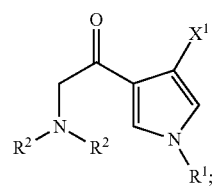
3 and thereafter
(c) reacting the compound 3 with the dihydroxy compound

in acid solution, wherein the linker between the hydroxyl groups is $C_1$-$C_6$ alkyl, to yield the compound 4

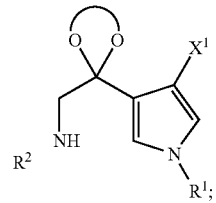
4 and
(d) reacting the compound 4 with the compound

in acid to produce the compound 5

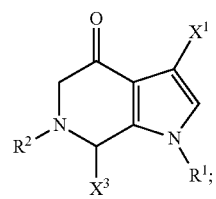
5

(e) contacting the compound 5 with Me-$X^4$ in base or MeO—$R^3$ in acid to produce the compound 6

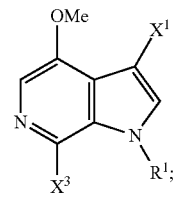
6 and then
(f) performing an oxidation reaction on compound 6 using [O] to yield the compound 7

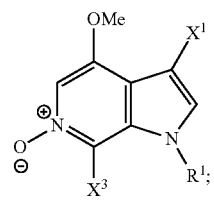
7 and
(g) performing an activation reaction to yield the resultant compound 10

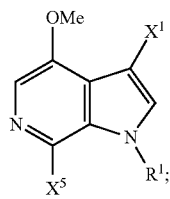
10 and then
(h) adding the triazolyl group 9

9 to compound 10 in the presence of Cu ion and a ligand to yield the compound of Formula (I) above wherein:

$R^1$=—H, -Boc, -Piv, —SO$_2$Aryl, —CH$_2$SAryl, —CH$_2$OP(O)(OR)$_2$, —CH$_2$OR, —CH$_2$Aryl;

$R^2$=each independently —H, —CO$_2$R, —SO$_2$Aryl, —CHO;

$R^3$=—H, —CO$_2$R, —CH$_2$SR, —CH$_2$OR, —CH(OR)$_2$, —CH(OR)(NR$_2$), —CH(NR$_2$)$_2$;

R=each independently —H, —C$_1$-C$_6$ alkyl, -aryl, —CH$_2$Aryl;

$X^1$=—H, —Cl, —Br, —I, $X^2$=—Cl, —Br, —I, —N(R$^2$)$_2$, —OSO$_2$R;
$X^3$ and $X^5$=each independently —H, —OR, —NR$_2$, —Cl, —Br, —I, —SR, —SO$_2$R, —SO$_3$R, —SR$_2^+$; and $X^4$=—Cl, —Br, —I, -OTs, +NR$_3$, pyridium, and The ligand is selected from the group of 1,2-diaminocyclohexane, trans-1,2-diaminocyclohexane, cis-/trans-diaminocyclohexane, cis-N,N'-dimethyl-1,2-diaminocyclohexane, trans-N,N'-dimethyl-1,2-diaminocyclohexane, cis-/trans-N,N'-dimethyl-1,2-diaminocyclohexane, 1,2-diaminoethane, N,N'-dimethyl-1,2-diaminoethane, 1,10-phenanthroline, 4,7-diphenyl-1,10-phenantroline, 5-methyl-1,10-phenanthroline, 5-chloro-1,10-phenantroline, and 5-nitro-1,10-phenanthroline.

In this further embodiment, it is preferred that R$^1$ is —SO$_2$Aryl. Aryl herein is preferably phenyl. It is also preferred that X$^1$ is —H. Additionally, it is preferred that X$^3$ is —H.

Also provided herein is a method of making the compound of Formula II which comprises:
(a) acylating the compound 10 using to yield the compound 11 and then
(b) reacting compound 11 with compound 13 in an activation reaction to produce compound 14 and
(c) adding the triazolyl compound 9 in the presence of Cu ion and a ligand to obtain compound 15

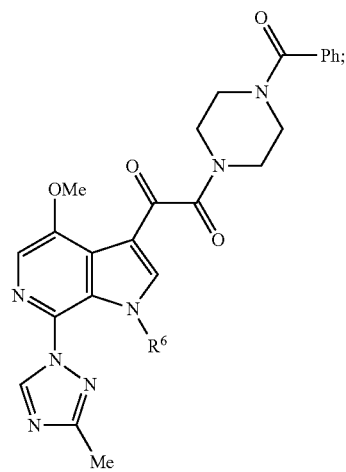

and
(d) reacting compound 17

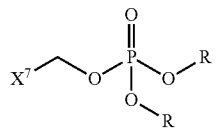

with compound 15 to produce compound 18

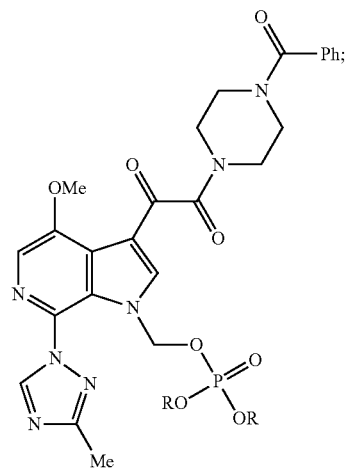

and
(e) conducting a functional group interconversion reaction to yield the compound of Formula II above; wherein:
R$^5$=—H, —OR, —NR$_2$, —Cl, —Br, —I, —SR;
R$^6$=—H, -Boc, -Piv, —SO$_2$Aryl, —CH$_2$SAryl, CH$_2$OP(O)(OR)$_2$, —CH$_2$OR, —CH$_2$Aryl, —Li, —Na, —K, —Ca, —Mg, TMG (Tetramethyl guanidine);
R=each independently —H, —C$_1$-C$_6$ alkyl, -aryl, —CH$_2$Aryl;

X$^1$=—H, —Cl, —Br, —I,

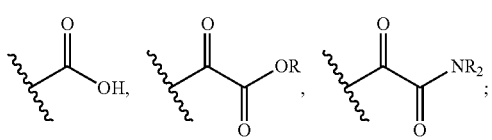

X$^5$=—H, —OR, —NR$_2$, —Cl, —Br, —I, —SR
X$^6$=—H, —OR, —NR$_2$, —Cl, —Br, —I, —SR, —SO$_2$R, —SR$_2^+$, —OSO$_2$R, —OSO$_3$R;
and X$^7$=—Cl, —Br, —I, —OSO$_2$R.

In this embodiment, the ligand may be selected as previously set forth. It is also preferred that R=tert-butyl, R$^6$ and X$^1$ are —H, and R$^5$ is —OMe. Aryl herein is preferably phenyl.

For a further embodiment of the invention, there is set forth process for making the compound of Formula III

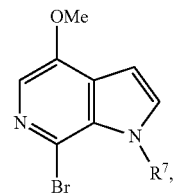
(III)

which comprises:
(1) reacting compound

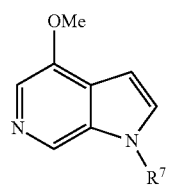
i with phthalic anhydride, H$_2$O$_2$ and dichloromethane to yield compound

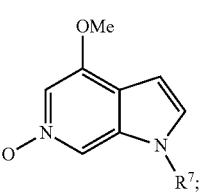
ii and
(2) conducting a PyBrop bromination reaction by reacting compound ii with PyBrop to prepare compound III,

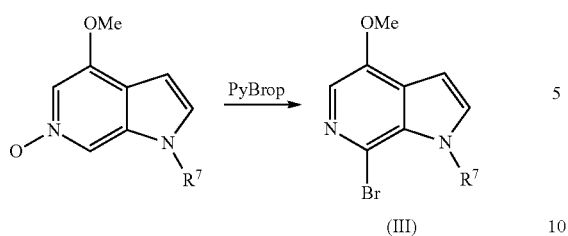

wherein R⁷=—H, alkyl, aryl, —SO₂R, —C(O)OR, and —C(O)NR₂; and wherein R=—H, —C₁-C₆ alkyl, aryl, —CH₂Aryl; and further wherein PyBrop is the peptide coupling reagent Bromo-tris-pyrrolidino phosphoniumhexafluorophosphate. Aryl herein is preferably phenyl.

In addition, the invention is also directed to a compound, including pharmaceutically acceptable salts and mixtures thereof, which is selected from the group of:

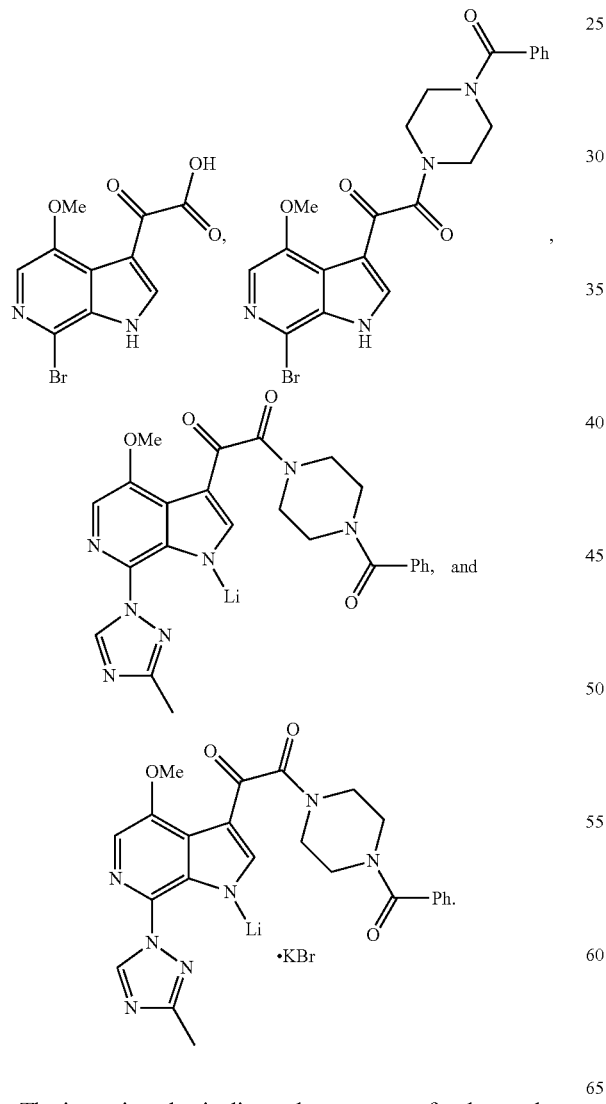

The invention also is directed to a process for the production of the compound

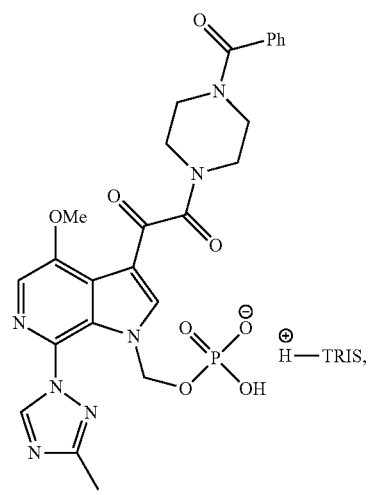

which comprises
(1) removal of the t-butyl groups from the compound

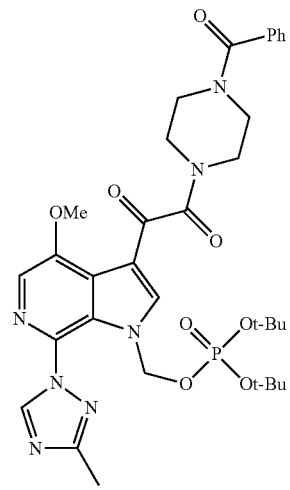 [SMILES: COc1cnc(-n2cnc(C)n2)c2c1c(C(=O)C(=O)N1CCN(C(=O)c3ccccc3)CC1)cn2COP(=O)(OC(C)(C)C)OC(C)(C)C]

using a solvent in the presence of water to obtain the compound

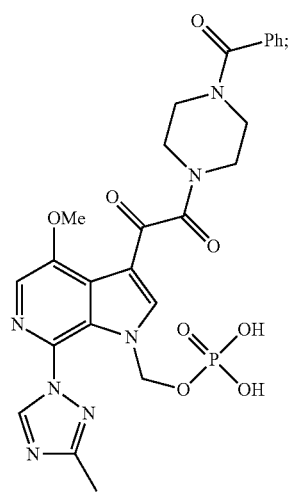 [SMILES: COc1cnc(-n2cnc(C)n2)c2c1c(C(=O)C(=O)N1CCN(C(=O)c3ccccc3)CC1)cn2COP(=O)(O)O]

and (2) reacting the compound

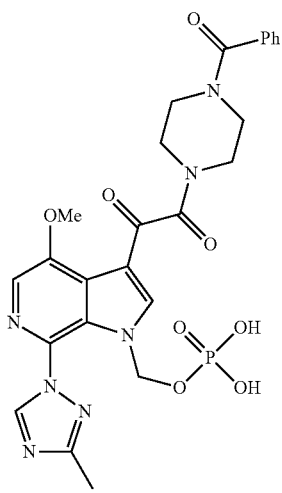 [SMILES: COc1cnc(-n2cnc(C)n2)c2c1c(C(=O)C(=O)N1CCN(C(=O)c3ccccc3)CC1)cn2COP(=O)(O)O]

with TRIS (tris(hydroxymethyl)aminomethane) and optionally a second solvent to obtain the compound

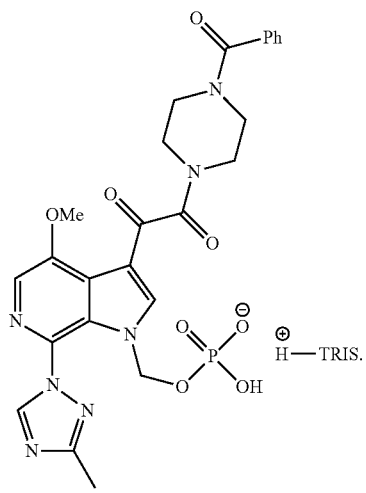

According to this process, the first solvent is selected from the group of carboxylic acid, NMP (N-methyl-2-pyrrolidone), DMSO, MeCN, MeOH, and acetone. The acid is selected from the group of $H_2SO_4$, $HNO_3$, HCl, phosphoric and carboxylic acids. The second solvent is selected from the group of water, alkyl ketone, heptane, toluene, ethyl acetate, DMSO, MeCN, MeOH and acetone. Even more preferably, the acid is acetic acid, and the second solvent is acetone.

The present invention is directed to these, as well as other important ends, hereinafter described.

DETAILED DESCRIPTION OF THE EMBODIMENTS

Unless otherwise specifically set forth, many reagents have been identified herein by their commonly accepted letter abbreviations in the art for ease of reference.

In addition, unless otherwise specifically set forth elsewhere in the application, the following terms may be used herein, and shall have the following meanings:

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted.

The term "$C_{1-6}$ alkyl" as used herein and in the claims means straight or branched chain alkyl groups with up to and including 6 carbon atoms, such as methyl, ethyl, propyl, isopropyl, butyl, isobutyl, t-butyl, amyl, hexyl and the like.

An "aryl" "Aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted.

In a preferred embodiment of the invention, the synthesis of the piperazine prodrug compound can be set forth in the following flow diagram:

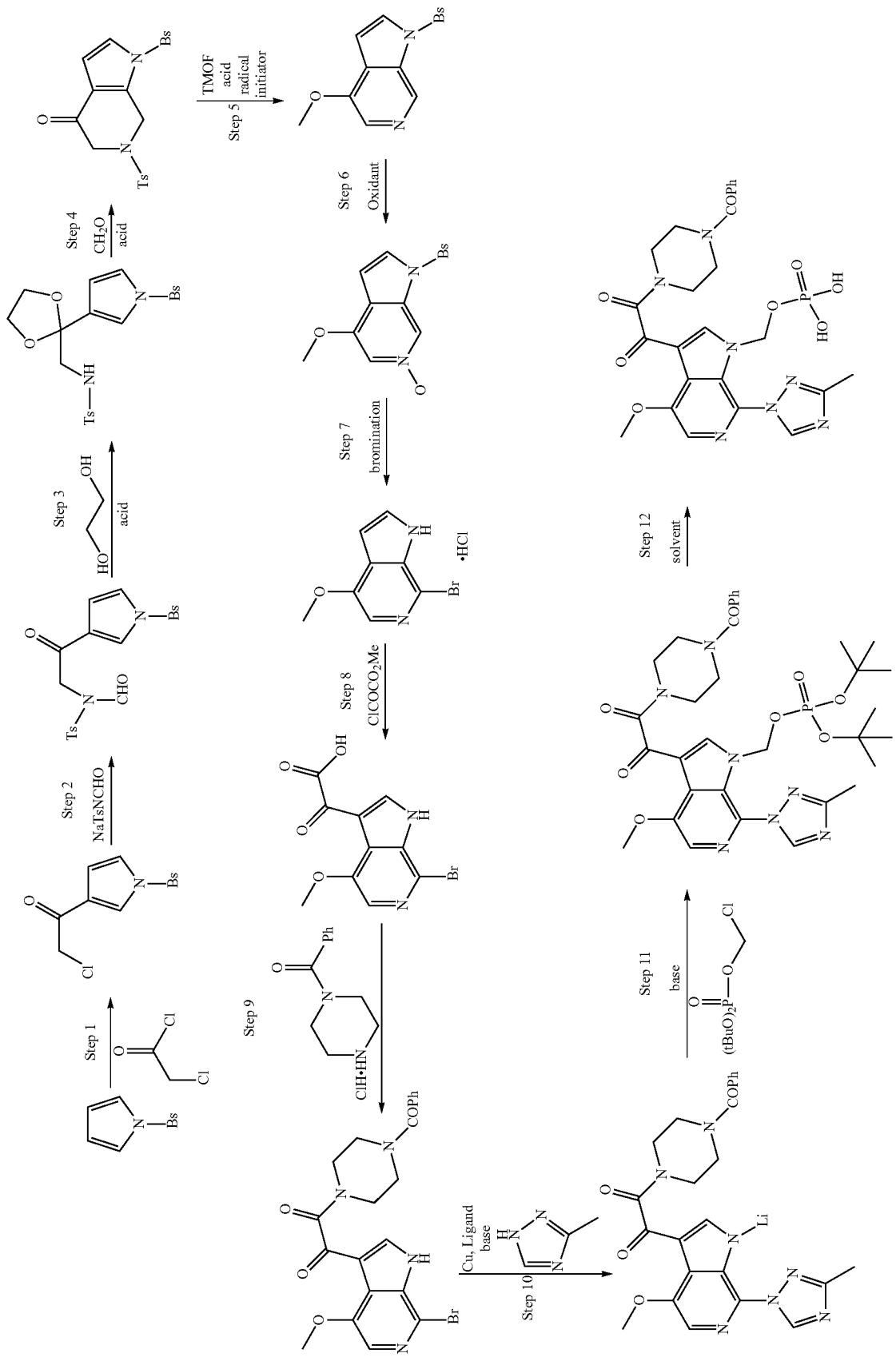

Even more preferably, as further set forth below, the synthesis of the piperazine prodrug compound begins from the N-sulfonylated pyrrole 1a. Friedel-Crafts acylation with 2-chloro acetyl chloride, in the presence of aluminum trichloride, provides the 3-acryl pyrrole derivative 2a. Displacement of the 2-choro ketone by the sodium salt of the N-formyl sulfonamide, in the presence of a tetraalkylammonium halide, preferably bromide, preferably tetrabutylammonium bromide, provides the amino-ketone 3a. Ketal protection of the ketone, in the presence of glycol and acid, results in the cleavage of the N-formyl protecting group and formation of the desired dioxalane 4a. A Pictet-Spengler cyclization with a formaldehyde equivalent, catalyzed by acid, provides the ketone 5a, which is treated with trimethyl orthoformate (TMOF) and acid in the presence of a radical initiator such as AlBN or cumene hydroperoxide to give the 6-azaindole 6a. Oxidation of the pyridine nitrogen provides the N-oxide 7a which is then treated with PyBrop in the presence of base, which brominates the C7-position, yielding the bromo-azaindole 8a after hydrolysis of the sulfonyl protecting group. A second Friedel-Crafts acylation onto C3 of the indole provides the oxalate 9a, which is coupled with the N-benzoyl piperazine to give the amide 10a. Addition of the triazole is catalyzed by copper, in the presence of an appropriate ligand and base, to give the indole 11c which is isolated as its lithium salt (or optionally as a co-salt with KBr). Alkylation of the indole nitrogen with the chloro-phosphate 14a gives the phosphate ester 12a, and subsequent solvolysis of the tert-butyl groups provides the final compound 13a.

Thus, the production of the piperazine prodrug compound may be shown more precisely as follows:

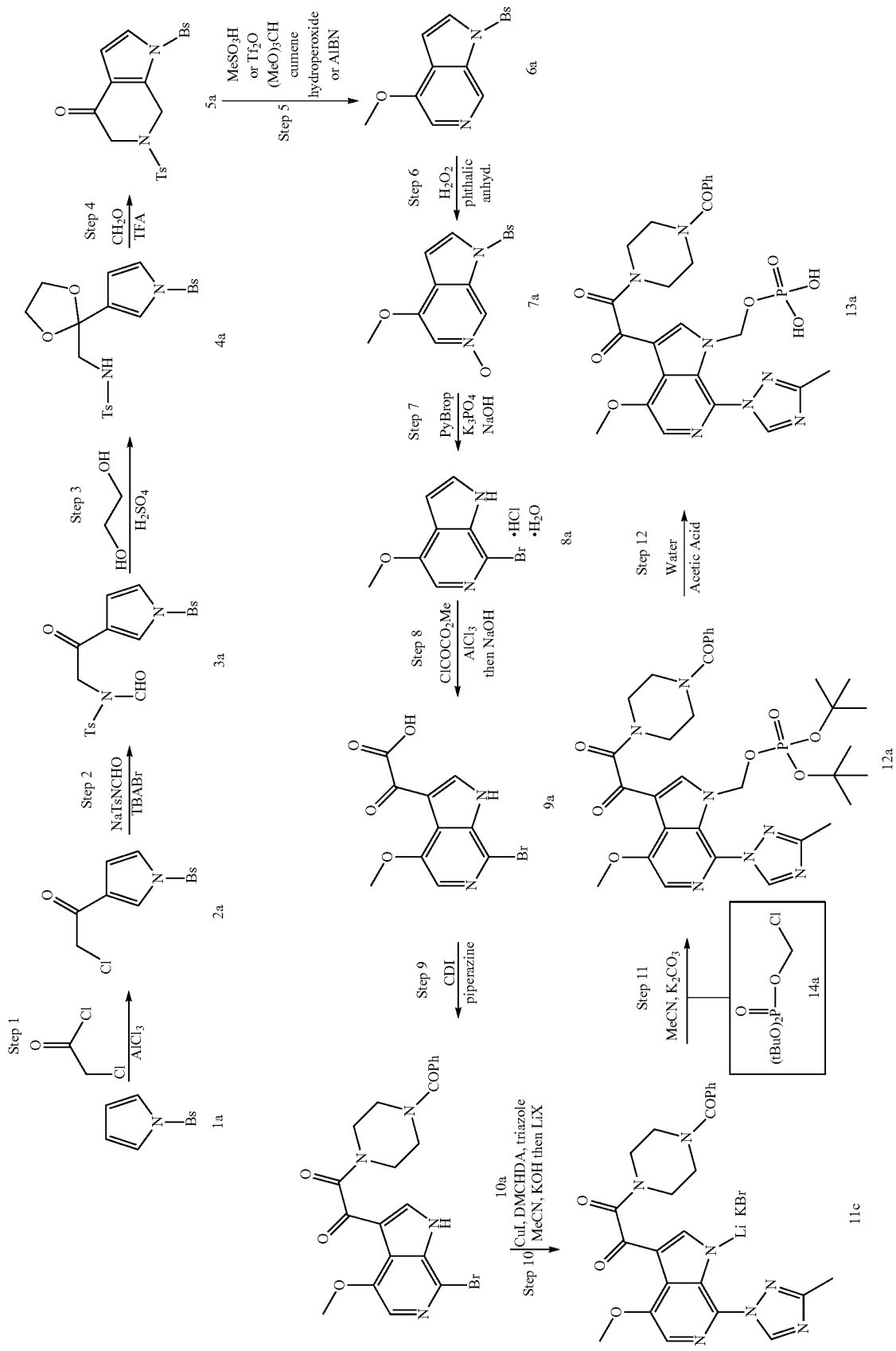

The foregoing description is merely illustrative and should not be understood to limit the scope or underlying principles of the invention in any way. Indeed, various modifications of the invention, in addition to those shown and described herein, will become apparent to those skilled in the art from the foregoing description and examples. Such modifications are also intended to fall within the scope of the appended claims.

What is claimed is:

1. A process for preparing the compound (I)

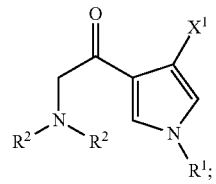

which comprises:

(a) reacting the compound 1

1

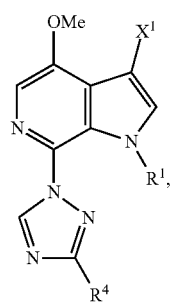

with the acid chloride compound

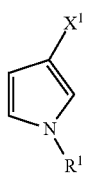

to form the compound 2

2

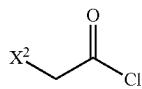

and then (b) contacting the compound 2 with a di-substituted amine $(R^2)_2NH$ in base to produce the compound 3

3

and thereafter (c) reacting the compound 3 with the dihydroxy compound

in acid solution, wherein the linker between the hydroxyl groups is $C_1$-$C_6$ alkyl, to yield the compound 4

4

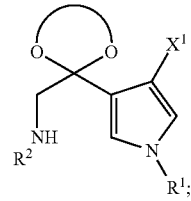

and (d) reacting the compound 4 with the compound

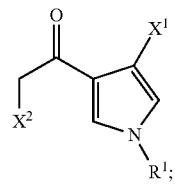

in acid to produce the compound 5

5

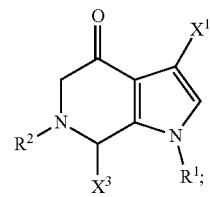

(e) contacting the compound 5 with Me-$X^4$ in base or MeO—$R^3$ in acid to produce the compound 6

6

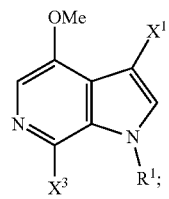

and (f) then performing an oxidation reaction on compound 6 to yield compound 7

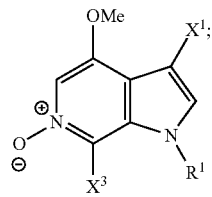

5

7 and (g) adding the triazolyl group

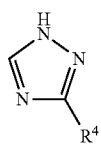

8 to compound 7, and then conducting a functional group interconversion reaction, to obtain the compound (I) above wherein:

$R^1$=—H, -Boc, -Piv, —SO$_2$Aryl, —CH$_2$SAryl, —CH$_2$OP(O)(OR)$_2$, —CH$_2$OR, —CH$_2$Aryl;

$R^2$=each independently —H, —CO$_2$R, —SO$_2$Aryl, —CHO;

$R^3$ and $R^4$=each independently —H, —CO$_2$R, —CH$_2$SR, —CH$_2$OR, —CH(OR)$_2$, —CH(OR)(NR$_2$), —CH(NR$_2$)$_2$, (C$_1$-C$_6$) alkyl;

R=each independently —H, —C$_1$-C$_6$ alkyl, -aryl, —CH$_2$Aryl;

$X^1$=—H, —Cl, —Br, —I,

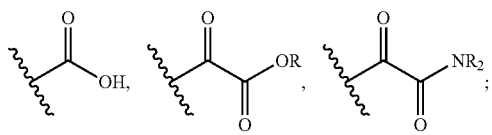

$X^2$=—Cl, —Br, —I, —N(R$^2$)$_2$, —OSO$_2$R $X^3$=each independently —H, —OR, —NR$_2$, —Cl, —Br, —I, —SR, —SO$_2$R, —SO$_3$R, —SR$_2^+$;

and $X^4$=—Cl, —Br, —I, OTs, +NR$_3$, -pyridium, and

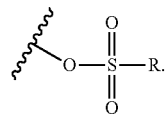

2. The process of claim 1, wherein $R^1$ is —SO$_2$Aryl.
3. The process of claim 2, wherein $X^1$ is —H.
4. The process of claim 3, wherein $X^3$ is —H.

5. A process for preparing the compound

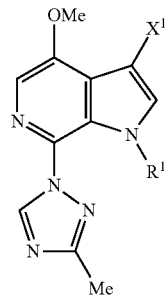

(I)

which comprises:

(a) reacting the compound 1

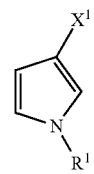

1 with the acid chloride compound

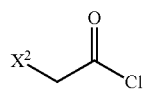

to form the compound 2

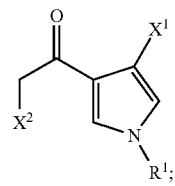

2 and then (b) contacting the compound 2 with a di-substituted amine (R$^2$)$_2$NH in base to produce the compound 3

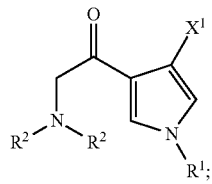

3 and thereafter
(c) reacting the compound 3 with the dihydroxy compound

5 in acid solution, wherein the linker between the hydroxyl groups is $C_1$-$C_6$ alkyl, to yield the compound 4

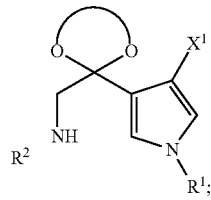
4 and
(d) reacting the compound 4 with the compound

in acid to produce the compound 5

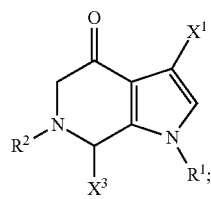
5

(e) contacting the compound 5 with Me-$X^4$ in base or MeO—$R^3$ in acid to produce the compound 6

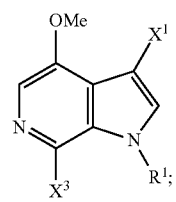
6 and
(f) then performing an oxidation reaction on compound 6 to yield the compound

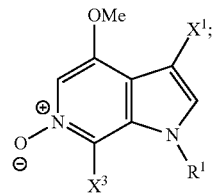
7 and
(g) adding the triazolyl group 9

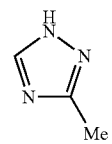
9 to compound 7, to obtain the compound (I) above wherein:
$R^1$=—H, -Boc, -Piv, —SO$_2$Aryl, —CH$_2$SAryl, —CH$_2$OP(O)(OR)$_2$, —CH$_2$OR, —CH$_2$Aryl;
$R^2$=each independently —H, —CO$_2$R, —SO$_2$Aryl, —CHO;
$R^3$=—H, —CO$_2$R, —CH$_2$SR, —CH$_2$OR, —CH(OR)$_2$, —CH(OR)(NR$_2$), —CH(NR$_2$)$_2$;
R=each independently —H, —C$_1$-C$_6$ alkyl, -aryl, —CH$_2$Aryl;
$X^1$=—H, —Cl, —Br, —I,

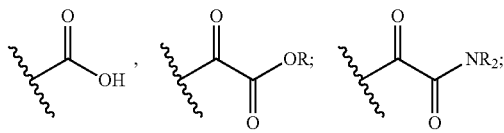

$X^2$=—Cl, —Br, —I, —N(R$^2$)$_2$;
$X^3$=each independently —H, —OR, —NR$_2$Cl, —Br, —I, —SR, —SO$_2$R, —SO$_3$R, —SR$_2^+$;
and $X^4$=—Cl, —Br, —I, -OTs, +NR$_3$, -pyridium, and

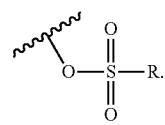

6. The process of claim 5, wherein $R^1$ is —SO$_2$Aryl.
7. The process of claim 6, wherein $X^1$ is —H.
8. The process of claim 7, wherein $X^3$ is —H.

* * * * *